United States Patent
Perry

(10) Patent No.: US 11,010,807 B1
(45) Date of Patent: May 18, 2021

(54) SYSTEM AND METHOD FOR IN PERSON HAIR CARE PRODUCT CREATION AND CUSTOMIZATION

(71) Applicant: Yvonne Perry, Westminster, CO (US)

(72) Inventor: Yvonne Perry, Westminster, CO (US)

(*) Notice: Subject to any disclaimer, the term of this patent is extended or adjusted under 35 U.S.C. 154(b) by 56 days.

(21) Appl. No.: 16/580,913

(22) Filed: Sep. 24, 2019

Related U.S. Application Data

(60) Provisional application No. 62/735,465, filed on Sep. 24, 2018.

(51) Int. Cl.

| | |
|---|---|
| G06Q 30/06 | (2012.01) |
| A61Q 5/00 | (2006.01) |
| A61Q 5/02 | (2006.01) |
| A61Q 5/12 | (2006.01) |
| A61Q 5/06 | (2006.01) |
| A61Q 5/04 | (2006.01) |
| A61Q 5/08 | (2006.01) |
| A61Q 5/10 | (2006.01) |

(52) U.S. Cl.
CPC .......... *G06Q 30/0621* (2013.01); *A61Q 5/00* (2013.01); *A61Q 5/06* (2013.01); *A61Q 5/12* (2013.01); *A61Q 5/002* (2013.01); *A61Q 5/004* (2013.01); *A61Q 5/006* (2013.01); *A61Q 5/008* (2013.01); *A61Q 5/04* (2013.01); *A61Q 5/065* (2013.01); *A61Q 5/08* (2013.01); *A61Q 5/10* (2013.01)

(58) Field of Classification Search
None
See application file for complete search history.

(56) References Cited

U.S. PATENT DOCUMENTS

| | | | | |
|---|---|---|---|---|
| 5,643,341 | A * | 7/1997 | Hirsch | A45D 34/00 8/405 |
| 6,594,642 | B1 * | 7/2003 | Lemchen | G06Q 10/06 705/26.5 |
| 7,899,713 | B2 * | 3/2011 | Rothschild | G06Q 30/0613 705/26.5 |
| 8,336,582 | B2 * | 12/2012 | Saranow | A45D 44/005 141/95 |
| 10,336,603 | B2 * | 7/2019 | Levenstein | B65D 83/64 |
| 2008/0004973 | A1 * | 1/2008 | Rothschild | G06Q 30/0613 705/14.46 |
| 2012/0023683 | A1 * | 2/2012 | Saranow | B01F 13/1055 8/405 |
| 2017/0174500 | A1 * | 6/2017 | Levenstein | B67D 7/0233 |

OTHER PUBLICATIONS

Anon., "Bath and Shower Products Market to Record Sturdy Growth by 202," M2 Presswire, Sep. 7, 201. (Year: 2018).*

* cited by examiner

*Primary Examiner* — Nicholas D Rosen
(74) *Attorney, Agent, or Firm* — Richard Eldredge; Leavitt Eldredge Law Firm

(57) ABSTRACT

A method of in person customization and creation of a hair care product, the method includes establishing a brick and mortar store, the brick and mortar store having an interior area with stations; creating a first station having one or more hair product bases; creating a second station having one or more add ins for hair care; and providing a container for an individual to create a customized hair care product within the container, the customized hair care product having one of the one or more hair product bases; the customized hair care product is based on the individual's hair care needs; and the one or more hair product bases and one or more add ins are composed of natural ingredients.

9 Claims, 4 Drawing Sheets

BASE — 301

- Aloe Vera
- Banana
- Coconut Milk
- Avocado
- Yogurt
- Flaxseed
- African Black Soap
- Liquid Castile Soap
- Apple Cider Vinegar
- Guar Gum
- Oatmeal
- Slippery Elm
- Marshmallow Root
- Mango Butter
- Shea Butter
- Cupuacu Butter

FIG. 3

Add Ins — 401

- Oregano oil
- Citrus Oil
- Thyme Oil
- Rosemary Oil
- Clove Oil
- Menthol
- Honey
- Egg
- Vegetable Glycerin
- Extra Virgin Olive Oil
- Coconut Oil
- Jojoba Oil
- Argan Oil
- Vitamin E Oil

FIG. 4

SYSTEM AND METHOD FOR IN PERSON HAIR CARE PRODUCT CREATION AND CUSTOMIZATION

BACKGROUND

1. Field of the Invention

The present invention relates generally to hair care product selection, and more specifically, to a brick and mortar store style hair care product creation system for creating customized hair care products.

2. Description of Related Art

Hair product selection systems are well known in the art and are effective means to purchase hair care products. For example, FIG. 1 depicts a conventional hair product purchase method 101, wherein an individual goes to a store and proceeds to purchase a hair care product based on packaging, ingredients, and the like, as shown with boxes 103, 105, 107, 109.

One of the problems commonly associated with system 101 is limited customization. For example, the individual has no control over the ingredients within each product and therefore must select a product that may only be partially suitable for them.

Accordingly, although great strides have been made in the area of hair product selection and purchase systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 3 is a simplified list of bases as shown in FIG. 2;

FIG. 4 is a simplified list of add ins as shown in FIG. 2; and

Figure 1:
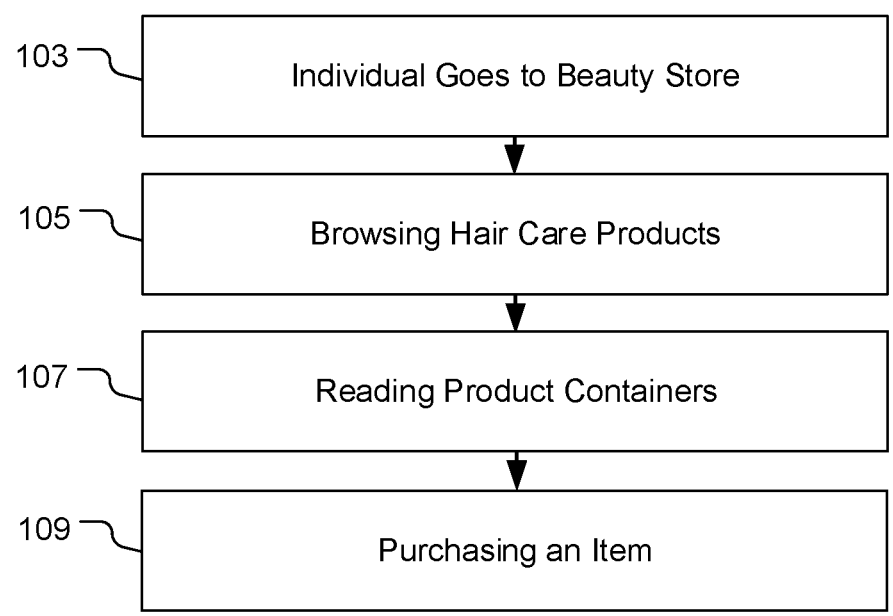
FIG. 1 is a flowchart of a common method of purchasing hair products.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional hair product purchasing systems. Specifically, the present invention provides for a system and method for an individual to create a hair care product in a store, wherein the hair care product is customized based on the needs of the user. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
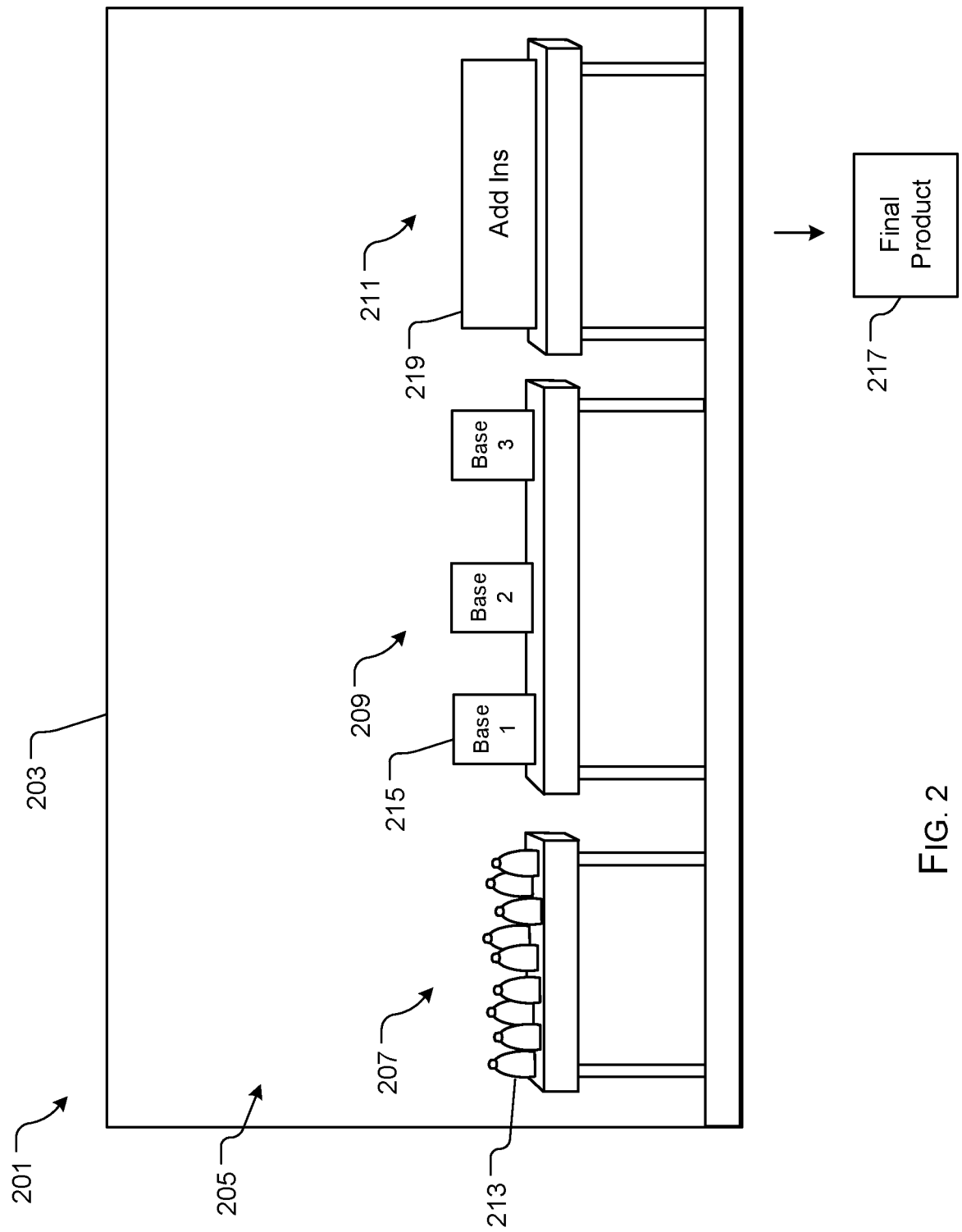
FIG. 2 is a simplified diagram of a system for in person hair care product customization and creation.

Referring now to the drawings wherein like reference characters identify corresponding or similar elements throughout the several views, FIG. 2 depicts a simplified diagram of a system 201 for the creation of hair care products in accordance with a preferred embodiment of the present application. It will be appreciated that system 201 overcomes one or more of the above-listed problems commonly associated with conventional hair product purchasing systems.

In the contemplated embodiment, system 201 includes a brick and mortar store 203 having an interior 205 with a plurality of stations 207, 209, 211. It should be appreciated that although the term stations is used herein, the stations are merely locations, groups, selections, or the like, and can be organized and designed in a plurality of manners according to the user.

In the preferred embodiment, a station 207 can include a plurality of containers 213 for use by an individual within the store. The containers 213 can vary in shape, size, and materials, and can further be reusable, such as if the individual returns to the store, it is contemplated that such a container can be composed of glass.

Another station 209 can include a plurality of bases 215, wherein the individual can begin the process of creating their own hair care product 217. The plurality of bases are considered to be beneficial for various hair types and various hair products, as will be discussed herein. It is contemplated that if an individual has a particular type of hair or particular need, a consultant could aid in picking the correct base for the desired product.

Another station 211 can include a plurality of add ins 219, wherein the individual (alone or with the guidance of a consultant) can select one or more add in items to add to their hair care product. The plurality of add in items could aid in moisture, volume, nourishment, or any other quality as desired.

It should be appreciated that one of the unique features believed characteristic of the present application is the system of having a brick and mortar store, wherein an individual can select from a desired base, and add in ingredients to create a completely customizable product. It should be appreciated that all of the bases and add in items are completely natural, thereby providing the user with a final product that is fully natural.

In FIG. 3, a contemplated list 301 of bases is shown. The bases to include one or more of: aloe vera, banana, coconut milk, avocado, yogurt, flaxseed, African black soap, liquid castile soap, apple cider vinegar, guar gum, oatmeal, slippery elm, marshmallow root, mango butter, shea butter, cupaucu butter. In FIG. 4, a contemplated list 401 of add ins is shown. The add ins to include one or more of: oregano oil, citrus oil, thyme oil, rosemary oil, clove oil, menthol, honey, egg, vegetable glycerin, extra virgin olive oil, coconut oil, jojoba oil, argan oil, and vitamin E oil.

Figure 5:
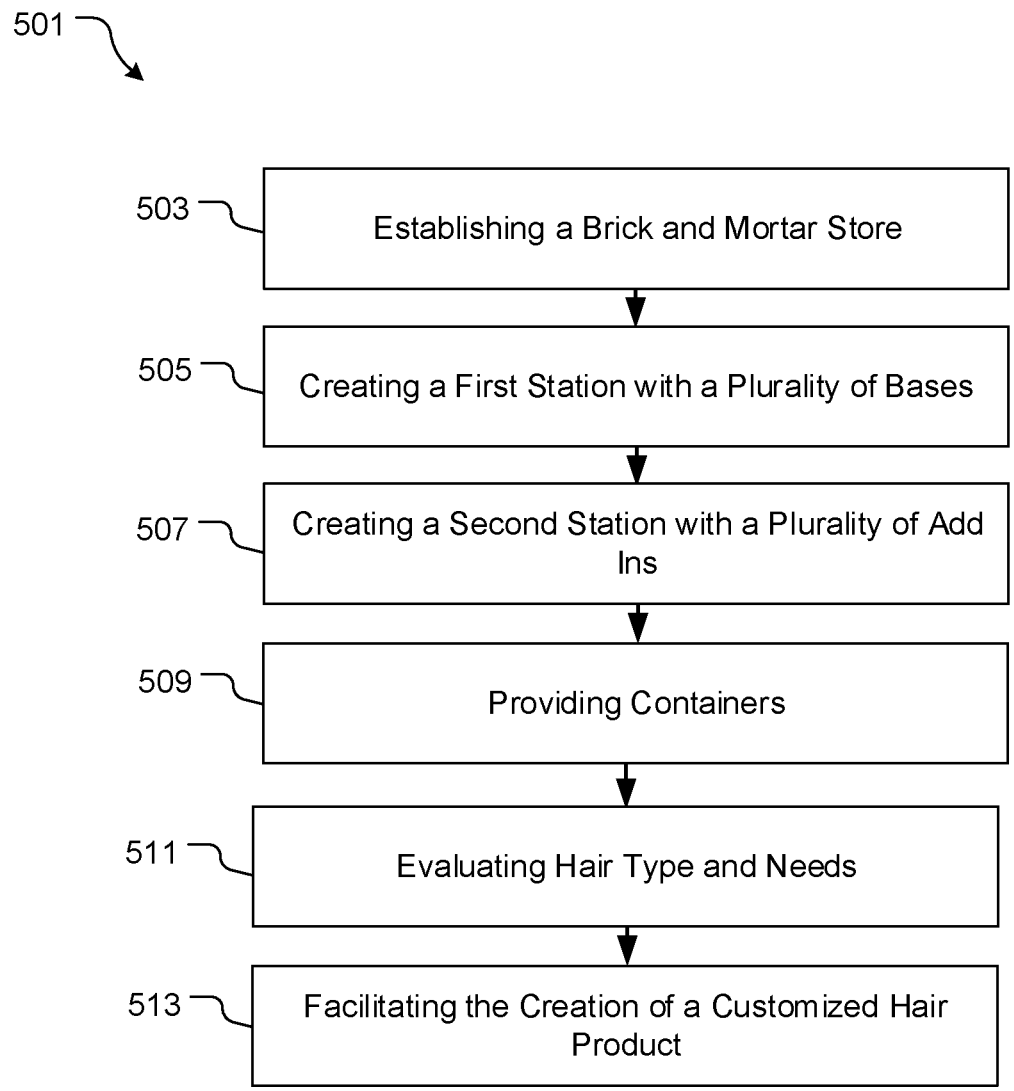
FIG. 5 is a flowchart of the method of use of the system of FIG. 2.

In FIG. 5, a flowchart depicts the method of use of system 201. During use, the brick and mortar store, having the plurality of stations, is established, as shown with boxes 503, 505, 507. An individual desiring to create a hair care product, such as shampoo, conditioner, gel, or the like, can then create a customized hair care product, with or without consultancy, and the resulting product to be stored within a container, as shown with boxes 509, 511, 513.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method of in person customization and creation of a hair care product, the method comprising:
   establishing a brick and mortar store, the brick and mortar store having an interior area with a plurality of stations;
   creating a first of the plurality of stations having one or more hair product bases;
   creating a second of the plurality of stations having one or more add ins for hair care; and
   providing a container for an individual to create a customized hair care product within the container, the customized hair care product having one of the one or more hair product bases;
   wherein the customized hair care product is based on the individual's hair care needs; and
   wherein the one or more hair product bases and one or more add ins are composed of natural ingredients.

2. The method of claim 1, wherein the one or more bases comprises:
   an aloe vera base;
   a banana base;
   a coconut milk base;
   an avocado base;
   a yogurt base; and
   a flaxseed base.

3. The method of claim 1, wherein the one or more add ins comprises:
   an extra virgin olive oil
   a coconut oil;
   a jojoba oil;
   an argan oil; and
   a vitamin E oil.

4. The method of claim 1, wherein the one or more add ins comprises:
   a honey;
   an egg; and
   a vegetable glycerin.

5. The method of claim 1, wherein the one or more bases comprises:
   an African black soap base;
   a liquid castile soap base; and
   an apple cider vinegar base.

6. The method of claim 1, wherein the one or more bases comprises:
   a guar gum base;
   an oatmeal base;
   a slippery elm base;
   a marshmallow root base;
   a mango butter base;
   a cocoa butter base;
   a shea butter base; and
   a cupuacu butter base.

7. The method of claim 1, wherein the container is a reusable container.

8. The method of claim 1, further comprising:
   evaluating the individual's hair to determine a hair type, the hair type being one or more of curly, dry, straight, wavy, thin, and thick;
   selecting one of the one or more bases based on the determined hair type; and
   selecting one or more of the one or more add ins based on the determined hair type.

9. The method of claim 1, wherein the one or more add ins comprises:
   an oregano oil;
   a citrus oil;
   a thyme oil;
   a rosemary oil;
   a clove oil; and
   a menthol.

* * * * *